US007178918B2

(12) United States Patent
Griffin

(10) Patent No.: US 7,178,918 B2
(45) Date of Patent: Feb. 20, 2007

(54) OPHTHALMIC LENSES WITH INDUCED APERTURE AND REDUNDANT POWER REGIONS

(76) Inventor: Richard A. Griffin, 12216 NW. 56 Ave., Gainesville, FL (US) 32653

( * ) Notice: Subject to any disclaimer, the term of this patent is extended or adjusted under 35 U.S.C. 154(b) by 0 days.

(21) Appl. No.: 10/970,272

(22) Filed: Oct. 21, 2004

(65) Prior Publication Data
US 2005/0068494 A1    Mar. 31, 2005

Related U.S. Application Data

(63) Continuation-in-part of application No. 10/234,993, filed on Sep. 4, 2002, now abandoned, which is a continuation-in-part of application No. PCT/US01/28156, filed on Sep. 6, 2001, which is a continuation-in-part of application No. 09/657,562, filed on Sep. 8, 2000, now Pat. No. 6,474,814.

(51) Int. Cl.
*G02C 7/04* (2006.01)
*A61F 2/16* (2006.01)

(52) U.S. Cl. .................................. 351/161; 623/6.28

(58) Field of Classification Search ................ 351/161; 623/6.27
See application file for complete search history.

(56) References Cited

U.S. PATENT DOCUMENTS

| | | | | |
|---|---|---|---|---|
| 5,112,351 | A * | 5/1992 | Christie et al. | 623/6.28 |
| 6,231,182 | B1 * | 5/2001 | Guilino et al. | 351/159 |
| 6,286,956 | B1 * | 9/2001 | Oyama et al. | 351/161 |
| 6,789,896 | B2 * | 9/2004 | Morris et al. | 351/159 |

* cited by examiner

*Primary Examiner*—Jordan M. Schwartz
(74) *Attorney, Agent, or Firm*—Sven W. Hanson

(57) ABSTRACT

Multifocal and single focus lenses are defined by nonconical aspheric optical surfaces. Various alternative surface shapes provide one or more vision regions bounded by optical steps. Each optical step has rapidly and smoothly changing power in the radial direction which creates an induced aperture through which the cortical elements of the human vision system are induced to concentrate. The induced aperture results in increased clarity and enhanced vision. In various configurations, the induced aperture decreases spherical aberration to further enhance vision. To increase correction intensity at one or more powers, redundant power regions are provided in repeated optical steps or annular apertures. In several embodiments, the redundant power regions create multiple induced apertures at one or more optical powers directed at one or more vision distances.

28 Claims, 14 Drawing Sheets

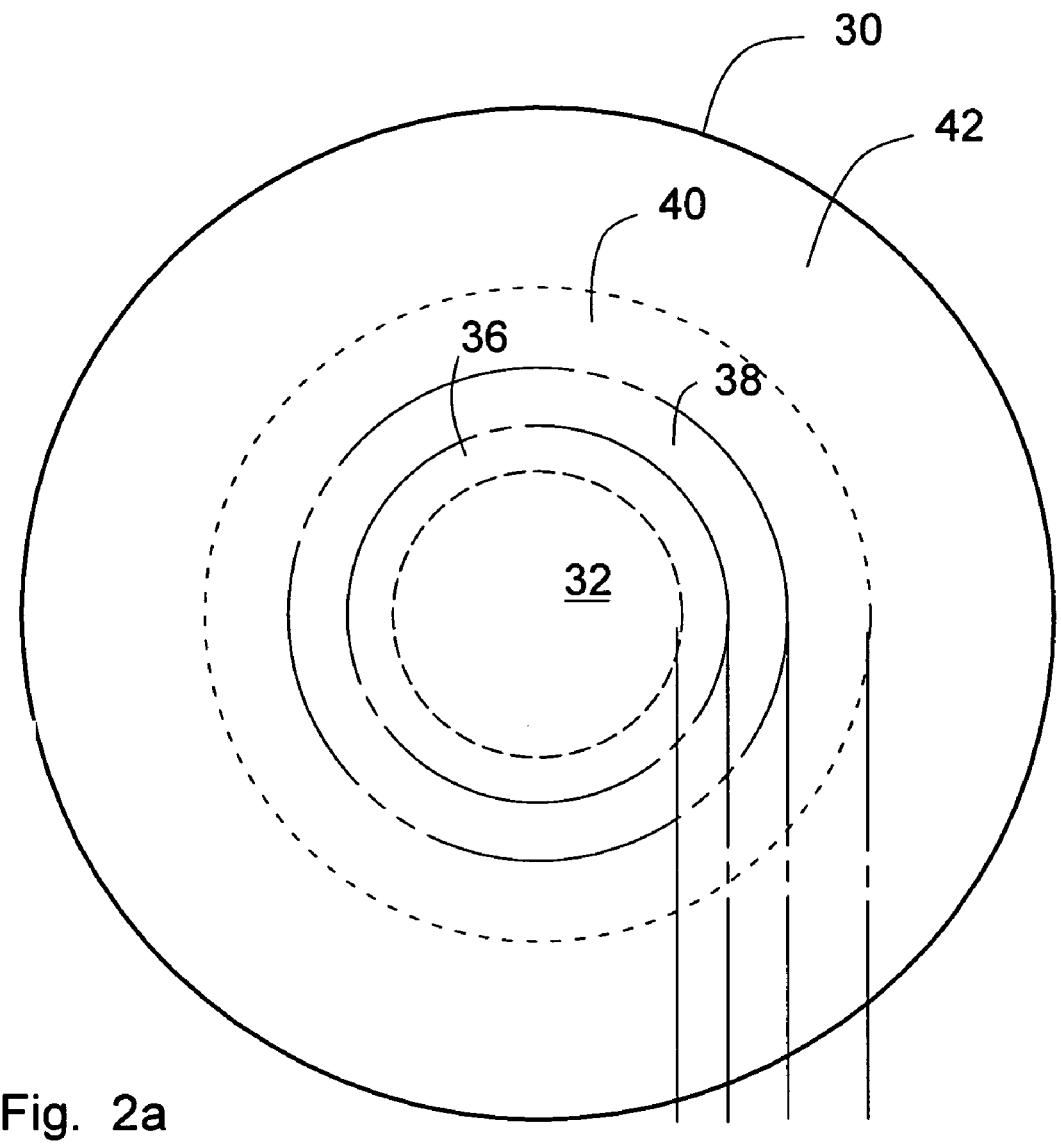
Fig. 2a
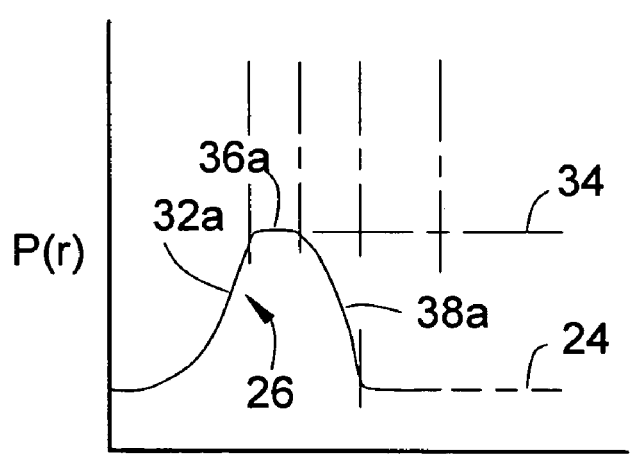
Fig. 2b    Radial Dimension

OPHTHALMIC LENSES WITH INDUCED APERTURE AND REDUNDANT POWER REGIONS

RELATED APPLICATIONS

The present application claims priority from, and is a continuation-in-part of, U.S. application having Ser. No. 10/234,993 filed Sep. 4, 2002 now abandoned which is a continuation-in-part of both U.S. application having Ser. No. 09/657,562 filed Sep. 8, 2000 and issued Nov. 5, 2002 as U.S. Pat. No. 6,474,814 B1 and International application No. PCT/US01/28156 filed Sep. 6, 2001.

BACKGROUND OF THE INVENTION

The present invention relates to ophthalmic lenses having more than a single focal length. The methods and structures provided are applicable to proximal and spectacle lenses and other lenses for correcting human vision.

The majority of vision-correcting lenses are designed to correct sight solely for distance viewing—with a single focal length. When a person views near objects, the eye accommodates the divergent, rather than parallel, light arriving from the near object. The act of accommodation by the human eye results in a physical change in shape of the crystalline lens within the eye, the flexure of this lens causes the incoming divergent light emitted by near objects to re-converge and focus on the retina. Accommodation increases the convergence of light waves by causing the lens surfaces to be more steeply curved, which in turn adds focal power to the optical system of the eye. The closer an object is viewed, the greater the accommodative demand placed on the eye. As the human crystalline lens ages, it slowly loses its gel-like flexibility. Although the process goes unnoticed for the better part of four decades, the lens body expands in girth and hardens, losing the ability to change shape with a resulting loss in accommodative ability. This condition is known as presbyopia. Typically, corrective lens wearers begin to notice presbyopia near the end of the fourth decade and then begin to require more than one lens in order to see clearly and efficiently at all distances. The convergent focal power requirement of this multiple lens system then typically increases gradually over the next fifteen years.

Early versions of multiple corrective spectacle lens systems for the human eye simply added an additional spectacle lens below the distance lens and designated the two-lens system a bifocal. The additional focal power afforded by this arrangement was known as the add-power for near vision. Eventually a third lens was placed between these two lenses to improve vision at intermediate distances, and the system became a trifocal. Because of recent innovations in the field of ophthalmic lens design, spectacles are now available in multifocals that are made in a continuous array of focal powers. These spectacles are made to accommodate the eye for distances from infinity to the reading plane, and are known as progressive-addition lenses. Although multifocal spectacle lenses have been largely successful in satisfying the needs of spectacle wearers, multifocal lenses that are positioned on or in the eye (proximal lenses): contact lenses, intra-ocular lenses and the alternative surgically imparted corneal lenses have been much less successful. Many recently emerging presbyopes are life-long wearers of contact lenses that correct only the distance vision. As presbyopia develops, most of these patients are forced to wear reading glasses over their contact lenses or to wear a distance lens in one eye and a near lens in the opposite eye (mono-vision). These two modes are very inconvenient, and sometimes hazardous to the wearer. Wearers of the so-called mono-vision modality must necessarily forfeit the natural binocular function that is needed to judge depth. Another growing population in need of multifocal correction is the pseudo-aphakic post-cataract surgery patient whose natural lenses have been replaced with implanted polymeric lenses. These patients must wear spectacles for reading after successful surgery, but many of them could benefit if the implanted lenses were efficiently shaped multifocals. Such a multifocal implant must be capable of replacing the variable focusing ability of their youthful natural lenses. Yet another large and growing group of lens wearers are the recent recipients of corneal surgery who find themselves forced to wear reading glasses after a very expensive surgical procedure that corrects only the distance vision. If corneal surgery could introduce a multifocal into the corneal stroma of proper shape and focal power distribution, it would alleviate the necessity of wearing reading spectacles in post-operative presbyopes.

Previous attempts to provide multifocal power to the human eye using contact lenses or other proximal lenses (those on or in the eye) have had limited success. Mimicking the simple bifocal spectacle, the device as described in U.S. Pat. No. 4,693,572 to Tsuetaki, et. al. is an example of segmented alternating bifocal contact lenses. This type of lenses must be caused to translate on the cornea of the wearer by pressure from the sensitive lower lid margin when the wearer gazes downward. Despite the discomfort of the lip pressure, this design has experienced some niche success. That success comes in part from the wide field of vision afforded the wearer as the pupillary aperture is exposed to a very large component of either the lower (near) lens or the (upper) distance lens in the two positions of gaze.

More recent designs, as found in U.S. Pat. No. 5,436,678 to Carroll depend upon the phenomenon of simultaneous focus to obtain addition power along with distant vision correction. Using this method, multiple foci: far, near and intermediate are presented within the pupillary zone at the same time. These devices depend upon discrimination by the cortical vision system to select the best focus available for the distance that is being viewed. Though this approach has had considerable success, most designs can correct only moderate amounts of presbyopia and are usually most successful when the surface shape treatment is applied to the corneal side of rigid gas-permeable contact lenses. In these designs, extreme curvatures are applied to the base curve, often creating metabolic problems for the cornea. The devices of the Carroll patent are modified in U.S. Pat. No. 5,835,187 to Martin to include a plurality of spherical zones on the front surface while maintaining conic curves on the posterior surface so that multifocal addition power is obtained from both surfaces. Unfortunately, the spherical zones are pieced together and are not a continuous array or radii with continuous first and second derivatives, with the result that diffraction will play a roll in degrading the optical performance of these lenses.

Various shapes have been applied to lens surfaces to improve simultaneous focus lenses. Aspheric multifocal lenses have been designed using multiple zones of conicoid surfaces. In concentric designs such as contact lenses or intra-ocular lenses, adjacent surfaces of revolution of differing shapes are smoothed mathematically to develop addition power that increases radially on the lens surfaces. Conicoids evolved as usable shapes for ophthalmic lenses primarily because of their variable shape and innate ease of manipulation. Consequently, aspheric contact lenses evolved from these conic functions. Though highly effective in generating variable foci, lenses designed around conic shapes do not always provide acceptable optics for the eye and can be somewhat unwieldy when used with interconnecting lens surfaces. Examples of more successful bifocal (not multifocal) lenses are discussed in U.S. Pat. Nos. 5,448,312 and 5,929,969 to Roffman. The Roffman bifocal is generated by alternating rings of two radii, one for distance power and another for near power in such a way as to maintain excellent near power for typical pupil sizes and ambient light conditions. Distance vision suffers from diffractive effects caused apparently by the centermost rings that surround the distance power zone, and by the loss of light and optical clarity created by the grooves between radii. An improvement on this design would seek to use an aspheric central and intermediate zone with alternating rings in only the outer add-power zone.

In most multifocus lenses adjacent power zones have boundaries which induce diffraction and other optical aberrations which degrade visual acuity. Various smoothing and transition methods have been developed to reduce this problem. U.S. Pat. No. 5,815,236 to Vayntraub discloses use of a logarithmic function in defining smoother transitions between lens zonal curves. U.S. Pat. No. 4,640,595 to Volk discloses using a variable shape (e-value) in smoothing conicoid surfaces. U.S. Pat. No. 5,452,031 to Ducharme discloses use of piece-wise polynomials or splining techniques to smooth zonal curve transitions. Unfortunately, the optical areas taken up by these transitions are at best wasted for vision correcting benefit and typically still introduce unfocused regions that reduce overall visual clarity. Optical discontinuities and ineffective transitions are particularly problematic within or adjacent to lens regions used for distance vision where they are more perceptible to the user than within near vision regions. Clear distance vision requires clear optics and the preponderant myopic population will not tolerate distance blur. Good pupil economics is also essential for the success of any lens placed on or within the eye itself. Given the limited size of the pupillary aperture, an array of lenses introduced to the eye-optical system must be applied with great precision and without wasted or unused optical area.

Other devices have been studied for the improvement of distance vision. The ability of the eye to see distance more clearly with a relatively fixed small aperture is well known. Consequently, methods of correcting distance vision have been proposed that use pinholes devices or similar small aperture designs. U.S. Pat. Nos. 3,794,414 to Wesley and 5,192,317 to Kalb provide examples of this approach. Although benefits can be gained for correcting presbyopia, most of these designs suffer from defects caused by diffraction at the edge of a dark ring or masked area, a phenomenon that detracts from any possible improvement obtained from these small aperture designs. In addition, the perimeter masking that is used to create these devices precludes multifocal functioning that is desired for correcting presbyopia.

Lenses made according to the above mentioned patents and methods reflect the optical limitations resulting from a large number of requirements for clear human vision at all distances and under a wide range of light conditions. These conditions can be more nearly met if the special attributes and abilities of the eye are fully utilized and applied economically within the limited pupillary zone. Uniquely, the human vision system is comprised of a rather simple optical device that often needs optical correction because of its diminutive size and organic changes. This rudimentary device is yoked to a complex cortical vision system that can control and suppress blurred areas advantageously if presented with carefully designed optics. What is needed is a method of forming an ophthalmic lens providing multiple focal lengths without loss of optical efficiency or acuity from ineffective transition regions, particularly adjacent distance vision regions. Preferably, such a lens also effectively creates a small aperture to improve viewing at any distance without the problems inherent to typical small aperture devices.

SUMMARY OF THE INVENTION

The present invention defines single focus and multifocal ocular lenses providing optical power for correcting vision over a continuous range from infinity to near sight distances. In a lens power distribution, radial optical steps are introduced having rapidly changing power. The optical steps produce enhanced vision in part by inducing an effective aperture, the image through which the cortical elements of the vision system are induced to concentrate. The enhanced vision effect of the induced aperture is applied to single focus and multiple focus lenses. One or more apical and/or annular induced apertures are used in various configurations to address specific correction requirements. In each configuration, the various induced apertures may have common or distinct minimum or maximum powers in the power distribution. Each such distinct power addresses correction for a specific plane-of-regard. In addition, the repeated nature of the power distribution provides redundant correction points within the optical steps which are integrated by the cortical system to increase acuity for intermediate distances distinct from the planes-of-regard addresses by the induced apertures. In this way, continuous correction may be provided by the inventive lens.

In certain embodiments, the optical surface shape producing the induced aperture power distribution also reduces spherical aberrations over conical shaped lenses adding to the enhanced vision effect. In one such embodiment, a positive lens having a single annular induced aperture is applied as a enhanced vision single focus lens.

In exemplary embodiments, cyclic power functions defining nonconical aspheric optical surfaces, are used to produce the desired optical power distributions. Cyclic power functions have benefits in ease of manipulation to fit various specific design requirements. The smooth and continuous nature of the power distributions used ensures no diffraction or other blurring effects exist in the mesopic pupillary region. The surface functions may be provided in form of polynomial series for simplicity of use in computer driven lathes for shaping contact lenses. For the same purpose, the power and surface functions may be reduced to representative tabular values.

The present power distributions are applicable to contact lenses, scleral lenses, intraocular lenses, and lenses impressed or surgically shaped within the corneal tissue. Equations are provided for creating anterior optical surfaces having the desired properties. However, optical devices generating the defined power distributions from posterior surfaces are also contemplated. Although nominally positive power lenses are also within the present invention, negative lenses gain particular benefit due to decreased lens thickness at the lens perimeter and consequent reduced spherical aberration. Spectacle lenses may also be defined using the power distributions of the present invention, although without the benefit of an effective aperture.

The present invention includes also methods of fitting lenses in which equations defining lens surface shapes are manipulated to produce a lens to meet specific user geometry and performance needs. Additional benefits and advantages of the present invention will become clear from the following detailed examples and associated figures.

DESCRIPTION OF THE DRAWINGS

FIG. 2a depict a contact lens according to present invention.

FIG. 2b is a graph of optical power as a function of radius for the embodiment of FIG. 2a.

DESCRIPTION OF THE PREFERRED EMBODIMENTS

Figure 1:
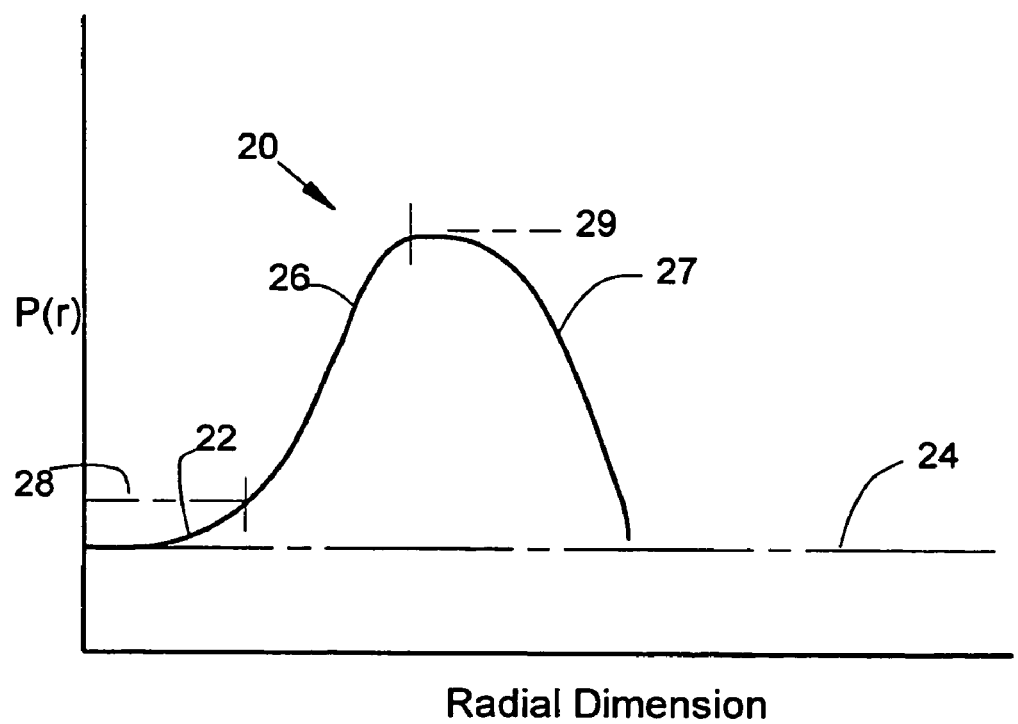
FIG. 1 is a graph of optical power as a function of radius for one embodiment of the invention.

FIG. 1 depicts a plot of the local optical power distribution 20 as a function of radial dimension from an apex of one embodiment of the invention. The vertical axis is optical power P(r) while the horizontal axis is radial dimension from the apex. A centrally located distance vision region 22 has a distance correction power which is effectively approximated by the apical power 24. The distance correction power is that power required to correct vision for viewing of objects infinitely distant. The required distance correction power may vary with the specific requirements of the users. Focal power increases gradually with increasing radius in the distance vision region 22 until a design level power 28 is reached. The incremental power addition from the apical power 24 (distance vision power) to the power addition that causes blur at the entrance pupil margin is defined here as the design level 28. The incremental power that causes blur in most persons is found to be between +0.25 and +1.25 diopters (meters$^{-1}$) and the design level power is selected to be in this range. The variation in power addition for the design level power is a result, in part, of the somewhat subjective analysis of what is considered blurred vision. For example, if the design level power value chosen by the lens designer is +0.50, and the nominal distance power in the central region is +1.00 diopter, then the effective aperture is that region bounded by +1.50 diopters of power. From the design level 28, the power rapidly increases with radius in what is termed an optical step 26. The rise in the power in the optical step 26 is sufficiently high that, during distance viewing, the cortical aspect of a user's vision system is unable to resolve through the surrounding blur of the optical step 26. As a result, the user is induced to view distant objects solely through the distance vision region 22. The perceived effect is similar to that known to be achieved by small aperture devices such as pinholes devices. The optical device having this effect, resulting from the combination of the distance vision region and surrounding optical step, is referred to here as an induced effective aperture. Unlike pinhole devices and masked apertures, the present effective aperture is not bounded by an opaque area which reduces the light entering the pupil. The effective aperture of the present invention is surrounded by regions functioning optically for vision correction upon attempted focusing at distances closer than infinity. The boundary and dimension of the effective aperture is not precisely definable as it is determined in part by a subjective cortical response. However, the bounds of the effective aperture can be approximated by the design level 28. As this region is circular in shape in the embodiment of the figure, the effective aperture can be quantified as twice the radial dimension to the design level 28. For greatest effect, the diameter of the effective aperture should be in the range of 0.1 to 3.5 mm (millimeters). Due to limitations of the mechanics of centering on the eye, a practical minimum may be 0.5 mm.

The optical step includes continuously increasing local power from the design level 28 to a maximum power 29, therein providing corrective power associated with all distances from infinity to near sight distances. "Near sight" is generally considered in the art to be at distances of approximately 40 mm from the eye. The power above the apical power 24 is generally referred to herein as "add" power. The add power of the distance vision region is effectively zero by definition. The add power required to fully correct for near sight vision is usually in the range of 1.0 to 3.0 diopters, depending upon the age of the wearer and the specific near sight distance used by the wearer. Outside the optical step, the power drops smoothly in a reduced power region 27 to approach the apical power. The pupil diameter for mesopic vision, during moderate lighting levels, ranges from 3.5 to 4.0 mm (millimeters) for the average person. The distance vision region and optical step occurs within the dimensions of the mesopic pupil to be effective at normal light levels. In low light conditions the pupil typically opens to a diameter of about 6 to 8 mm. In low light conditions, distance correction rather than near sight correction is desired as distance viewing is the dominant mode in low light for most persons. For this reason it is often desired that the lens power be reduced in the region beyond the mesopic diameter of the pupil. The power distribution in the diminished light or scotopic zone takes various forms in alternative embodiments In one embodiment the scotopic zone power is more negative than the apical distance power. This is desirable due to the generally recognized increased negative correction required by most persons for night vision.

For clear vision at any plane-of-regard, the power distribution must be continuous within and proximate the bounds of the distance vision regions. To obtain the required power distribution it is necessary to form a lens surface shape having first decreasing and then increasing radius of curvature. In various embodiments of the present invention, this is obtained by using a catenary-like equation having combined exponential growth and decay functions. Optical surfaces based on catenaries have superior optical characteristics for multifocus lenses due to the occurrence of the centers of radius near the optical axes, rather than skewed from the axis as in the case of conic functions. The present invention manipulates the catenary-like equations by allowing the base of the function to vary from the natural logarithmic base.

The power distribution in FIG. 1 is produced on a lens anterior optical surface by a surface of revolution obtained from the following equation:

$$Z(x) = c_1 \cdot P^{kx} + c_1 \cdot P^{-kx} + c_2 \qquad \text{Eq. 1}$$

where:

$Z(x)$ is the sagittal depth from a common datum x is a perpendicular distance from the apex in millimeters k is the inverse of the apical radius of curvature; (mm$^{-1}$)

P is a variable exponential power base $c_1$, $c_2$ are coefficients determined by the known boundary conditions Equation 1 has continuous values from the apex to the limits of the effective lens area. The first and second derivatives are continuous as well. The apical radius of curvature is defined in the typical manner by the particular wearer's eye geometry, material properties, and the distance vision correction required. The constants $c_1$ and $c_2$ are determined from the known boundary conditions to be:

$$c_1 = (2 \cdot k \cdot (\ln P)^2)^{-1} \quad c_2 = (k \cdot (\ln P)^2)^{-1} \qquad \text{Eq. 2}$$

The power base P may be any positive number greater than 1 but is, for practical contact lenses, less than about 60, although in some cases P may be as high as 100. The values of P are dependent upon the units of measure and in these values are with respect to the equations herein expressed in millimeters. By using different values of P, the shape and maximum power of the power distribution shown in FIG. 1 is altered for a particular lens design. Preferably, to obtain useful near vision correction power, a P value is selected such that the value of the power distribution reaches the near vision power at or before the mesopic pupillary boundary. This ensures near vision correction is available to the user in normal light conditions. In order to obtain corrective power beneficial to the user for intermediate distances—between near sight and infinity—the power distribution first derivative should not be excessive. Practical upper limits on the slope of the power distribution are not known and may be user dependent. Proper modification selection of the power distribution, by modification or selection of the power base P, may necessarily be guided by empirical feedback obtained from the user. In some cases, increased clarity of vision at one distance may require sacrifice of clarity at a second distance. At P values which produce the required near vision power within the mesopic pupil the resulting power distribution typically rises radially well above the required add power.

Example contact lens designs according to the present invention are provided in Table 1 below for various combinations of parameters. These lenses are based on HEMA-based hydrogel having an index of refraction of 1.4.

TABLE 1

| Lens # | Near Add (diopters) | Distance Power (diopters) | P | Effective Aperture Dia. (mm) | Mesopic Pupil Dia. (mm) | Max Add (diopters) |
|---|---|---|---|---|---|---|
| 1 | 2.50 | −5 | 13.9 | 1.85 | 3.5 | 7.66 |
| 2 | 2.50 | +5 | 9.93 | 1.79 | 3.5 | 4.62 |
| 3 | 2.50 | −20 | 58.9 | 1.91 | 3.5 | 18.02 |
| 4 | 1.25 | −5 | 9.4 | 2.64 | 3.5 | 7.66 |
| 5 | 1.25 | +5 | 7.8 | 2.55 | 3.5 | 1.87 |
| 6 | 1.25 | −20 | 23.2 | 2.70 | 3.5 | 9.31 |

A base curve radius of 8.5 mm and a mesopic pupillary diameter of 3.5 mm was assumed in each case. The lenses were designed to have the near add power at this mesopic boundary. The effective aperture is calculated from a critical design power of +0.75 diopters above the distance power. The value of power in diopters in the above table and elsewhere herein is in meters$^{-1}$.

All but two of the above example lenses are negative power lenses (inducing increased divergence of incident light rays). A negative contact lens generally increases in thickness with increasing radius from the lens center. The thickness of the lens is known to produce spherical aberration which degrades clarity of vision capable with the lens. In each case above, the maximum add power of the lens is significantly greater than the required near add power. In each of the negative lenses, the maximum add is at least threes times the near add power. The surface shape that produces this high power outside the optical step also results in thinning of the lens at the perimeter. An advantage of the present design in negative lenses is a reduced thickness resulting when the surface shape defined by Equation 1 is applied to a lens anterior surface. This reduced thickness reduces spherical aberration and increase clarity for the user.

The optical step at the edge of the effective aperture is termed such because its rapid power rise is analogous to a "step" function between the distance vision region 22 and maximum power 29. To ensure clear vision it is necessary to create the optical step without discontinuities which might induce light diffraction or other unfocused alteration of incident light. Such effects are particularly deleterious when occurring in distance vision regions because the human eye is more sensitive to unfocused light in distance vision than in near vision. Prior methods of forming regions of different optical power that include such discontinuities do not provide optimum vision. Various methods previously suggested by others that require optically nonfunctional transitions or smoothing regions suffer from this detraction. It is desired in the present invention to provide an optical step as a smooth continuum of the lens power curve if optimum distance vision is to be obtained. The terms of Equation 1 are defined and continuous over the full range of the lens surface. By avoiding multiple discontinuous functions or shapes producing discrete power zones for distance vision, the consequent necessary transitions and their effects are avoided.

Equation 1 can be transformed by Taylor expansion into the following polynomial equation $$Z(x) = \frac{1}{2} \cdot k \cdot x^2 + \frac{1}{24} \cdot k^3 \cdot (\ln P)^2 \cdot x^4 + \qquad \text{Eq. 3}$$

-continued $$\frac{1}{720} \cdot k^5 \cdot (\ln P)^4 \cdot x^6 + \dots$$

which can also be expressed as the summation:

$$Z(x) = \sum_{n=1}^{m} \frac{k^{2n-1}(\ln P)^{2(n-1)}}{(2 \cdot n)!} \cdot x^{2n} \qquad \text{Eq. 4}$$

where the terms are as previously defined and m is less than 15 and preferably less than 5 for convenience of manufacture. This equation is convenient for lens design and fabrication operations. The rapid convergence of the power function of this invention requires use of as few as two terms of the above equation in many cases. Such surface equations expressed as polynomials are easily applied in computer lathing systems for machining lens surfaces or molds for casting lens surfaces. Similarly, these equations defining the present inventive lenses may be expressed in tables of discrete values of radius and associated sagittal dimension.

Mathematically, a surface of revolution must contain only even exponents as shown in the above form; however, modern computerized lens lathing systems are able to generate surfaces of revolution for odd exponents by utilizing the absolute values of those terms. This allows additional odd exponent terms to be added to the above equation to manipulate the result for design effect. Other polynomial expressions are possible to express the same basic function including expressions including fractional exponent terms. In addition, the first term of Equation 3 may be modified from its simple parabolic form to include other conic shapes which provide occasional benefit without detracting from the advantages of the power form. The following equation is a general expression of an alternative power distribution including a general conic term:

$$Z(x) = \frac{kx^2}{2} \cdot \left[1 - (1 - S \cdot k^2 \cdot x^2)^{1/2}\right] \cdot \qquad \text{Eq. 5}$$

$$\left[1 + (1 - S \cdot k^2 \cdot x^2)^{1/2}\right]^{-1} ++$$

$$(2 \cdot k \cdot (\ln P)^2)^{-1} \cdot P^{k \cdot x} + (2 \cdot k \cdot (\ln P)^2)^{-1} \cdot$$

$$P^{-k \cdot x} - (k \cdot (\ln P)^2)^{-1}$$

Where S is an asphericity or shape factor. For S=0, the entire first term vanishes to obtain the original exponential form of Eq. 1. The following conic shapes are defined in Eq. 5 by the value of S applied:

| Conic Shape | S Value |
| --- | --- |
| Hyperboloid | S < 0 |
| Paraboloid | S = 0 |
| Ellipsoid (prolate) | 0 < S < 1 |
| Ellipsoid (oblate) | S > 1 |
| Sphere | S = 1 |

Lenses produced using this equation and method have similar characteristics with the previous examples, but with the added degree of freedom provided by the included shape factor S which can be manipulated to change the size of the effective aperture and shape of the optical step.

Figure 3:
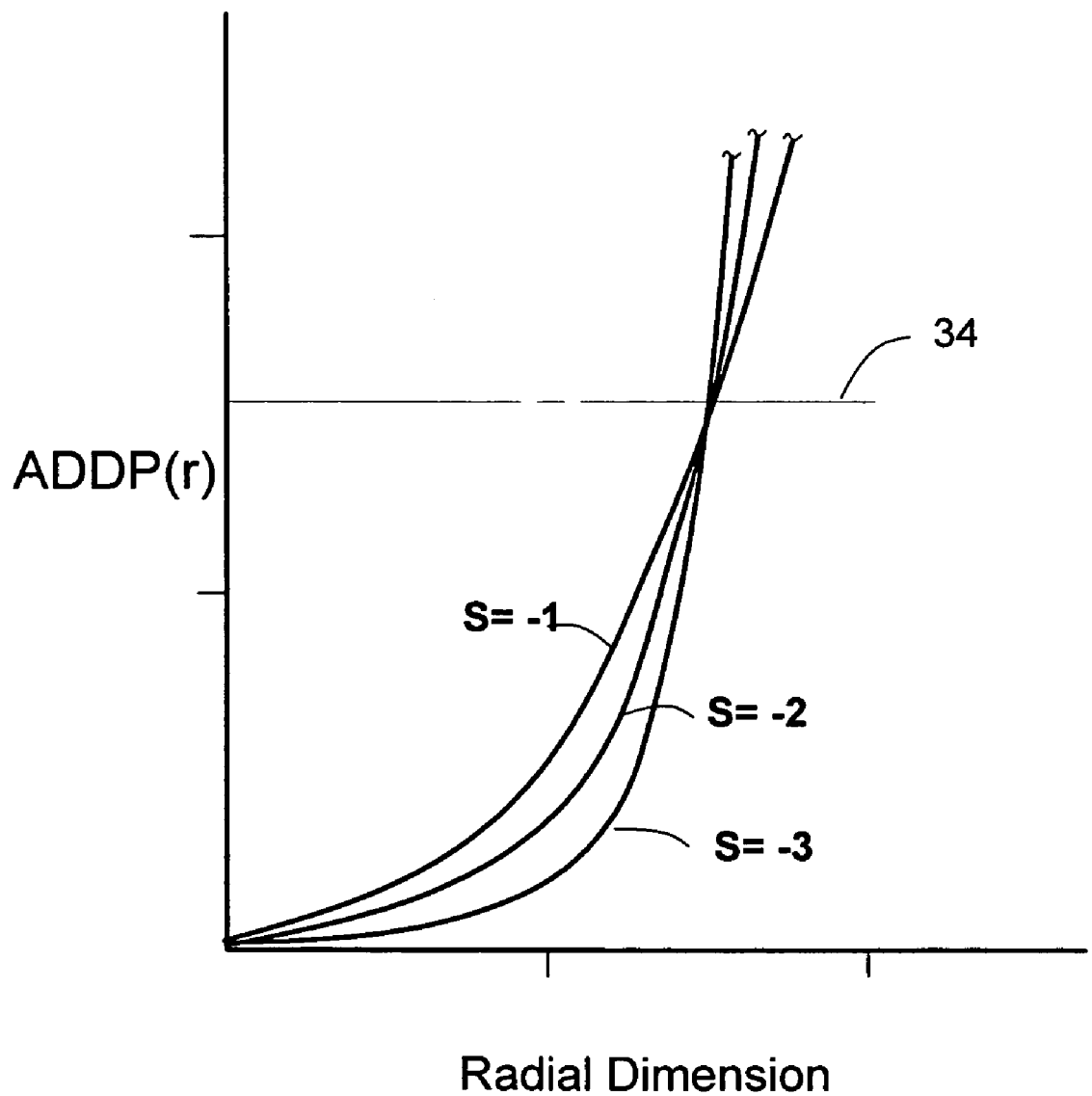
FIG. 3 are three graphs of optical power as a function of radius for an alternative power distribution equation having various values for a shape factor.

FIG. 3 contains graphs of add power for lenses defined by Equation 5 with various values of the shape factor S. For each power distribution shown, the value of P has been adjusted such that the power distribution passes through the near vision power 34 at the same radial dimension. By adjusting S and P in this manner, the shape of the optical step and slope of the power distribution between the distance vision region and the near vision power may be manipulated. For most contact lenses, the shape factor S will have a value in the range of −5 to 2. At S values beyond this range, the value of P becomes excessively small or large resulting in a distorted power distribution. Table 2 provides example lens designs according to the present invention with various values of S.

TABLE 2

| Lens # | Near Add (diopters) | Distance Power (diopters) | S | P | Effective Aperture Dia. (mm) | Mesopic Pupil Dia. (mm) | Max Add (diopters) |
| --- | --- | --- | --- | --- | --- | --- | --- |
| 7 | 2.50 | −5 | +1 | 7.17 | 1.86 | 3.5 | 7.32 |
| 8 | 2.50 | −5 | −1 | 22.4 | 1.90 | 3.5 | 10.44 |
| 9 | 2.50 | +20 | −2 | 19.5 | 2.56 | 3.5 | 10.67 |
| 10 | 1.25 | −5 | +1 | 4.1 | 2.64 | 3.5 | 4.35 |
| 11 | 1.25 | −5 | −1 | 16.3 | 2.72 | 3.5 | 5.55 |
| 12 | 1.25 | +20 | −2 | 17.9 | 3.21 | 3.5 | 8.43 |

As in the previous examples, a base curve radius of 8.5 mm and a mesopic pupillary diameter of 3.5 mm was assumed in each case. The lenses were designed to have the near add power at this mesopic boundary. The effective aperture is calculated from a critical design power of +0.75 diopters above the distance power.

Because the power distributions obtained from the above equations are typically continuously increasing at the near vision power, the area of the lens providing near vision power is also typically small. A consequence for some users may be reduced near vision clarity. To provide increased near vision correction in mesopic conditions, the power distributions above are modified outside the central distance vision region to enhance near vision correction. FIG. 2a depicts such a contact lens according to a preferred embodiment of the invention. FIG. 2b is a plot of the optical power of the lens of FIG. 2a as a function of radial dimension from the lens apex. The lens 30 includes central region 32 with a power distribution 32a corresponding to the distance vision region 22, and optical step 26, as shown in FIG. 1. The power distribution 32a is produced in various distinct embodiments by alternate application of the above equations. The focal power in the central region rises steeply in an optical step 26 to create an induced aperture as discussed above. The maximum power reached is the specifically required near vision power 34. At this power, the optical step is truncated and the near vision power 34 is maintained through an annular near vision region 36 extending outward from the central region 32. The central region 32 and near vision region 36 both lie within the mesopic pupillary dimension. In alternative embodiments, the near vision region 36 has a varying power distribution which follows various shapes to allow more smooth transition between the optical step and a transition region 38. From the outer perimeter of the near vision region 36, the optical power decreases rapidly in a transition region 38 to a power equal the apical power 24. Preferably, the outer perimeter of the transition region 38 is approximately at outer limit of the mesopic pupil. In this example the transition power distribution 38*a* in the transition region 38 follows a simple hyperbolic. It is important that the transition region be as smooth as possible so as to not introduce blurring, while at the same time retracing power rapidly so that a minimum of radial extent is used. Other curves may also accomplish these requirements, such as may be expressed by various polynomials. Radially outside the transition region 38 is a lens scotopic vision region 40 having distance vision power—apical power 24. As discussed above, in an alternative embodiment the scotopic vision region has a reduced power which is less than the apical power. Outside the scotopic region of the lens is an lenticular flange 42. The flange 42 does not provide optical effect, but provides physical support to the lens. It is important that any smoothing or blending that is required between the above regions is outside the primary distance vision zone which is within the central region. Such smoothing may be carried out in any of a variety of known methods.

Figure 4:
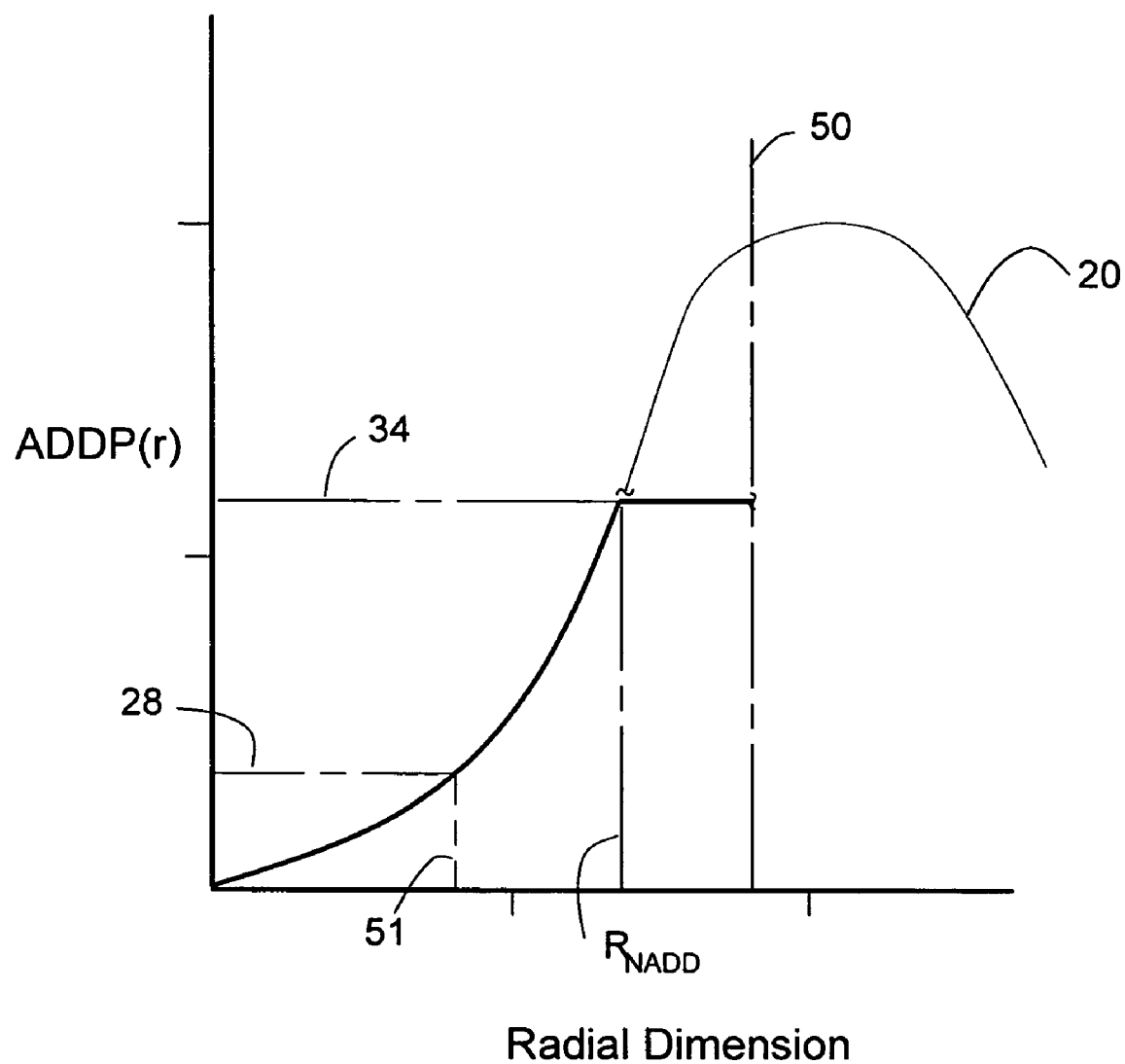
FIG. 4 is a graph of a power distribution of the present invention modified to balance distance vision with near sight vision.

In alternative embodiments, to provide balanced near and distant vision, the power distributions are manipulated to adjust the respective corrective areas on the lens. It is believed that a more effective combination of near vision and distance vision may be obtained by providing a region of near vision power at least as large as the distance vision power lens area. That is, using areas normal to the optical path, the area within the annular near vision region is equal or greater the area within effective aperture. Manipulation of both P and S is required to obtain the desired result from Equation 5. This can be carried out by an iterative process as now described with respect to FIG. 4 which is a graph of a power distribution 20. It is presumed that the user and lens specific parameters have been defined and inserted into Equation 5. The required near vision power is also determined from the user's requirements. A trial shape factor is selected: S=−1 is suggested. A first estimate of the near vision power radial dimension ($R_{NADD}$), less than the user's mesopic pupillary radial dimension 50, is chosen. Equation 5 is then evaluated for various P values and the resulting add power (ADDP(r)) calculated at $R_{NADD}$. When the power distribution at $R_{NADD}$ equals the required near vision power 34, the effective aperture 51 is determined from the equation and the selected design level (see above). This may be done by iterative trial and error. The respective areas of the near vision region and within the effective aperture are then calculated. If the near vision region is insufficient—less than within the effective aperture—the shape factor is decreased. If the near vision region is too large—greater than within the effective aperture—the shape factor is increased. Iteration on P may be used again to obtain the desired near vision power and verify the areas. In the lens produced from this method, the power distribution is truncated at the near vision power to form a near vision region 36 extending to the pupillary dimension 50 as described with respect to FIG. 3. The near vision region 36 has constant power over its area. The lens regions outside the mesopic pupil may be designed as described with respect to FIG. 3. The above iterative processes may be automated by computer methods. Tabulated values for common parameters may also be used to simplify the process. Other methods of executing these steps are also available to those skilled in the art.

Figure 5:
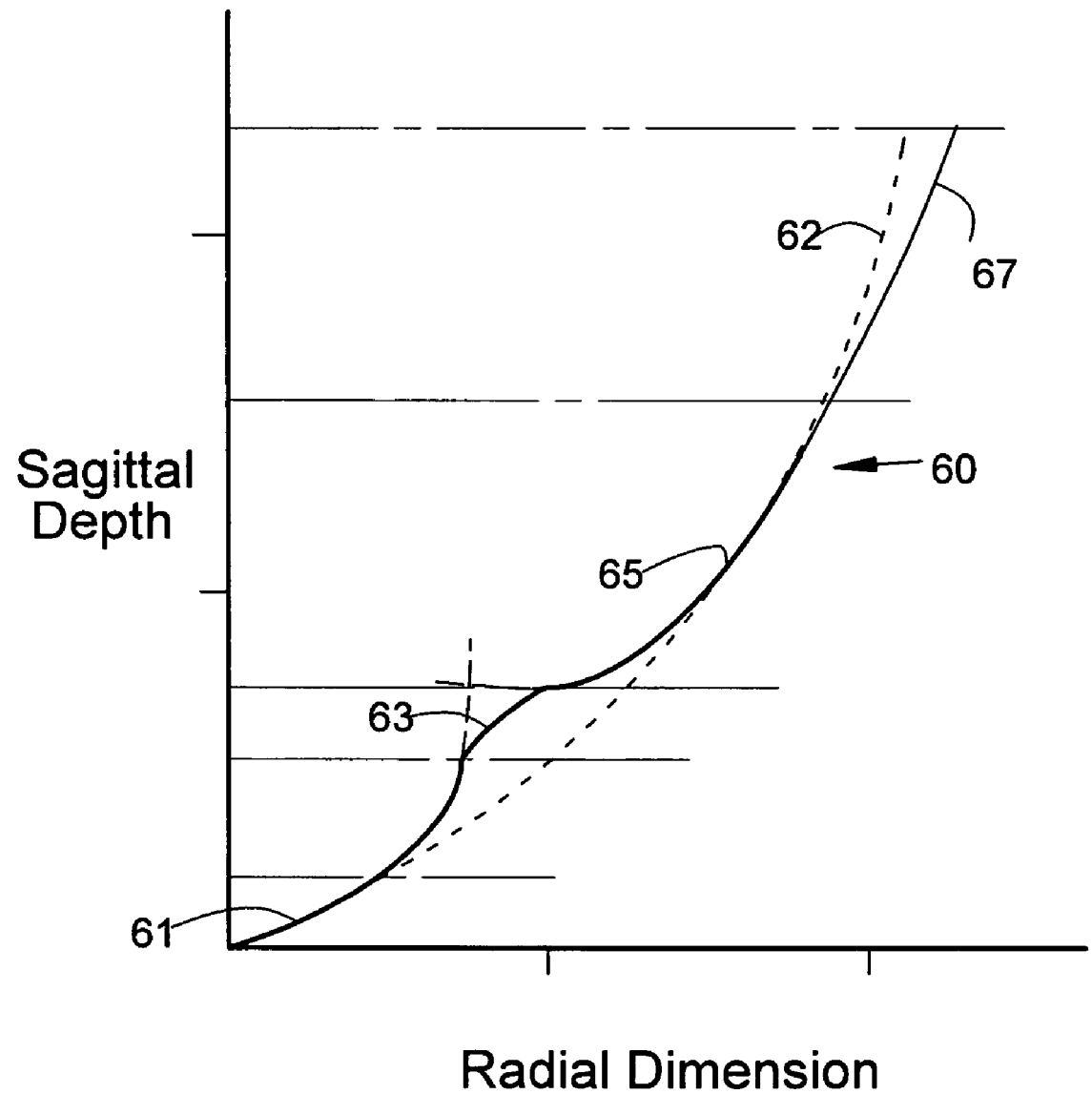
FIG. 5 is a graph of an optical surface of a contact lens according to one embodiment of the invention.

FIG. 5 is a graph of an optical surface corresponding to the power distribution and corrective regions depicted in FIG. 2*b*. From the apex, a central surface region 61 curves inward from a spherical reference line 62. The spherical reference line 62 corresponds to the surface of a single power lens. The central surface region 61 corresponds to the central vision region power distribution (32*a* in FIG. 2*b*). The central surface region 61 ends at a sulcus surface 63 corresponding to a near vision power. From the sulcus surface 63 extends a scotopic surface region 65 having increasing radius of curvature which corresponds to the transition and scotopic region powers. At the outer edge of the surface is a lenticular flange surface 67.

An approximation of the above power distributions is obtained in a distinct embodiment by use of cyclic functions which provide additional benefits. The following equation for a lens add power provides improved transition between the intermediate powers and the near vision power while also providing control of the maximum power and its radial location.

$$ADD(x) = \frac{ADDM}{2} \cdot \left[1 + \cos\left[\pi \cdot \left(\frac{Xc - x}{Xc}\right)\right]\right] \qquad \text{Eq. 6}$$

Where: ADD(x) is the add power at a point x as defined above, ADDM is the maximum power which is selected to be equal the required near vision power, and Xc is the desired location of the maximum power.

Figure 6:
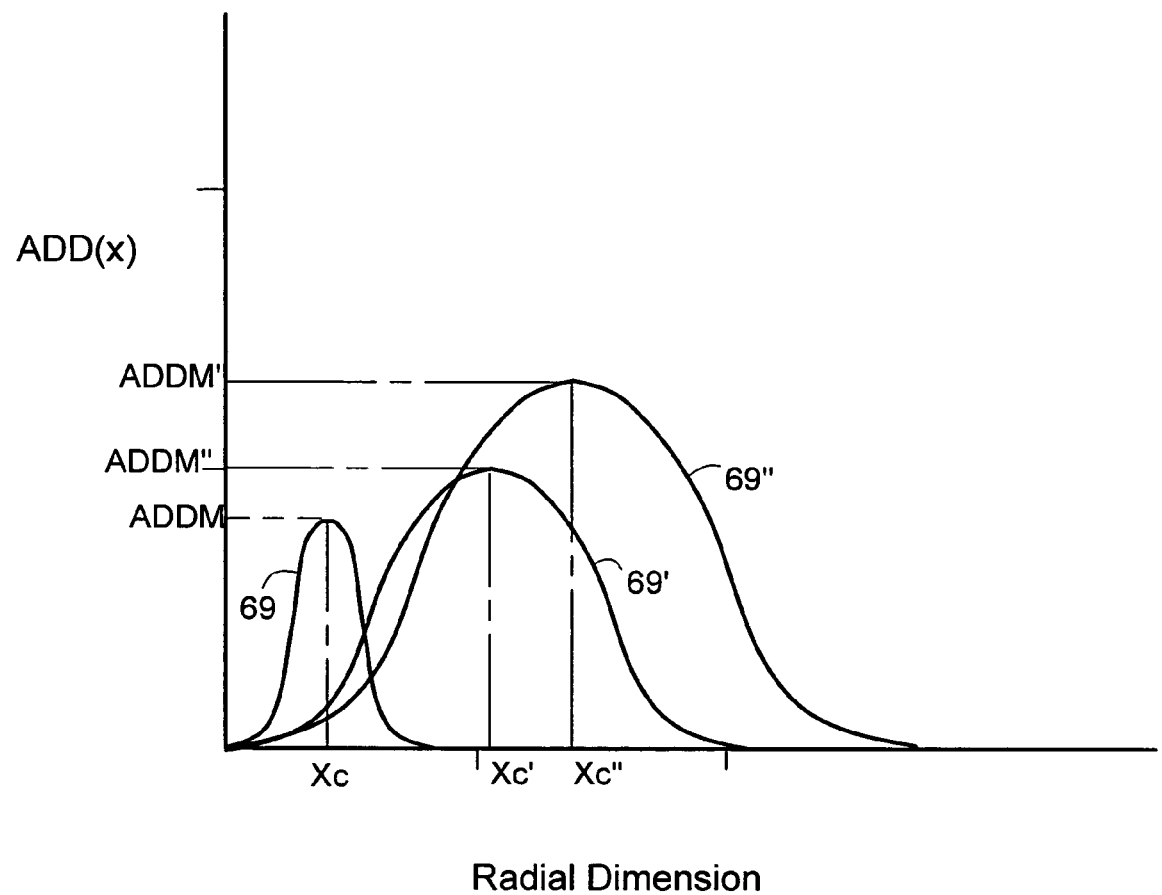
FIG. 6 is a graph of add power for various cyclical power distributions according to the present invention.
Figure 7:
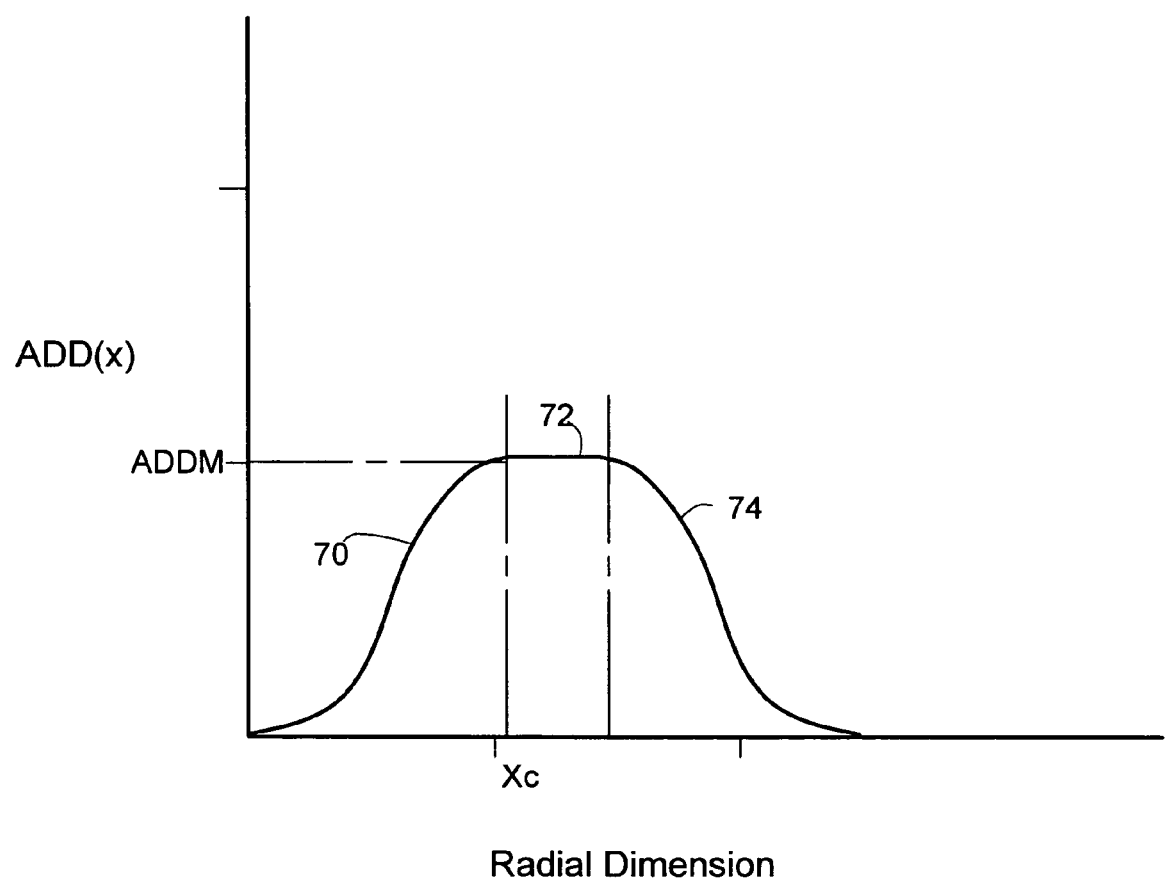
FIG. 7 is a graph of a cyclical power distribution used in an optical step and in a decreasing power transition region with an intervening near vision region.

FIG. 6 is a graph of power distributions 69, 69', 69" generated by this equation for various values of ADDM and Xc in the above equation. Lenses formed with these power distributions exhibit the same optical benefits provided by the effective aperture and optical step discussed previously. Due to the ability to control the maximum power of the distribution they are particularly well suited for modification by introduction of a extended near vision region in the manner of the previous embodiment. FIG. 7 depicts a lens power distribution formed by extending such a cyclic power distribution 70, from the maximum power ADDM, with a near vision region 72 having constant near vision power in the radial direction. The shape of the cyclic power distribution 70 provides a smooth transition to the near vision region and improves optical quality. A mirror image 74 of the cyclic power distribution 70 is used at the outer boundary of the near vision region 72 to define a smooth transition reducing optical power in the radial direction to the apical distance power.

The complete surface function can be derived for Equation 6, but results in an equation that is unwieldy to apply in manufacture of lenses. An effective approximation of the optical surfaces associated with the power distribution of Equation 6 can be developed from the following equation:

$$Z(x) = \frac{1}{2} \cdot k \cdot x^2 + \frac{M \cdot 10^{-3}}{2(n-1)} \cdot \left[\frac{1}{2} \cdot x^2 + \left(\frac{T^2}{\pi^2}\right) \cdot \left(\cos\left(\frac{\pi}{T} \cdot x\right) - 1\right)\right] \qquad \text{Eq. 7}$$

Where: M and T are variables which must be determined.

In order to arrive at the proper surface shape, Equation 7 is manipulated in the typical manner to arrive at a corresponding approximate power function in terms of M and T. Appropriate values of M and T are determined by iteration and comparison of the approximate power function shape with the desired power function of Equation 6. When the two power function shapes are sufficiently similar, the corresponding values of M and T are applied to Equation 7. This surface is then applied to create a lens optical surface producing the desired power function of Equation 6.

The above equations for optical surface shape generate the desired optical power distributions when applied to the anterior surface of a contact lens. Although they may be used to form positive lenses, additional benefits are obtained when used to form negative lenses as mentioned above.

Due to the small size of the centrally located distance vision region, it is desirable that the optical axis of the lens be centered, in use, with respect to the vision axis of the pupil. Currently available hydrophilic soft contact lenses generally center well on the eye and are therefore preferred for carrying out the invention over typical rigid lenses which generally do not center as well. However, in any contact lens that can be maintained in centered position, the concepts here are equally applicable. One method of improving lens centering with rigid gas permeable lenses uses a reverse geometry base similar to concepts known and used for corneal molding in orthokeratology. The reverse geometry base applies to the posterior surface of a lens a relatively flat curve centrally to the corneal apex and surrounds that region with a steepening radius portion that creates a suction to the cornea. Surrounding these regions is a third region having a curvature which aligns with the cornea. A combined effect of these features is a centering force applied to the lens. The surface shapes defined by the above Equations 1 and 5 can also be applied to the rigid gas permeable lens base curve and, utilizing these shapes' natural flat-steep-flat characteristics, provide the same centering effect.

In the above examples, it is presumed that the pupil's optics are centered on the pupil body geometric. This is often not the case as a natural geometric offset of the pupils is found in some persons. In order to position a contact lens eccentrically with respect to the pupil body geometry, in alternative embodiments an eccentric bevel is applied to the perimeter of the posterior surface. Similarly, an eccentric flange may be used for the same effect. By establishing a lens eccentricity, with respect to the pupil geometry, that equals the optical eccentricity, the lens may be centered with the optical axis. These embodiments are most effectively used in soft and rigid gas permeable lenses.

Contact lenses according to the present invention include hard, soft lenses, and rigid gas permeable lenses formed of any of the materials typically used. The preferred lens is a hydro-gel or silicone based hydro-gel soft lens. The optical power of a lens is a function of both the lens shape and material properties. The lens shapes and functions discussed herein are with respect to the lens' intended condition during use. This means, for example, that lenses designed with a significant water content are fully hydrated. Current lathe systems are capable of transforming input parameters to account for material properties changes such as occur in contact lenses having a high water content in use. Similarly, cast lenses can be formed taking into account the same material transformations.

Although the discussions above have been primarily with respect to contact lenses, the invention includes other lenses incorporating the novel concepts herein, including but not limited to, scleral lenses, intraocular lenses, and lenses impressed or surgically shaped within the corneal tissue. In particular, power distributions having optical steps creating effective apertures are formed in these alternative optical devices. In Table 3 below design parameters are given for an IOL and a formed corneal surface profile according to the present invention.

TABLE 3

| Lens | Near Add (diopters) | Distance Power (diopters) | S | P | Effective Aperture Dia. (mm) | Mesopic Pupil Dia. (mm) |
| --- | --- | --- | --- | --- | --- | --- |
| IOL | 2.50 | +20 | 0 | 18 | 1.83 | 3.5 |
| Corneal Profile | 2.50 | 0 | 0 | 10.1 | 1.80 | 3.5 |

In the IOL design the index of refraction of the lens and vitreous is presumed to be 1.49 and 1.34, respectively. The IOL is a "D" shaped lens with a center thickness of 0.50 mm. The corneal index of refraction is taken to be 1.376 with a 7.7 mm corneal radius. The details of forming such devices with the herein defined optical surfaces is known to those skilled in the art.

In an alternative embodiment, the benefits of the above adjustable power and surface functions are achieved in spectacle lenses. Due to their lack of proximity with the pupil, the effects of an induced aperture are lessened in spectacle lenses according to present invention. However, the above power and surface equations provide unique methods of forming progressive spectacle lenses where a first power distribution defines an umbilical line along one axis of the lens. Orthogonal power distributions are defined with coincident power values at the intersection points with the first power distribution on the umbilical line.

The effect of the induced aperture produced by the present invention is also of value to correct distance vision when near vision correction is not required. The present invention includes contact lenses having an optical step and induced aperture without a specific need for near sight correction.

Figure 8:
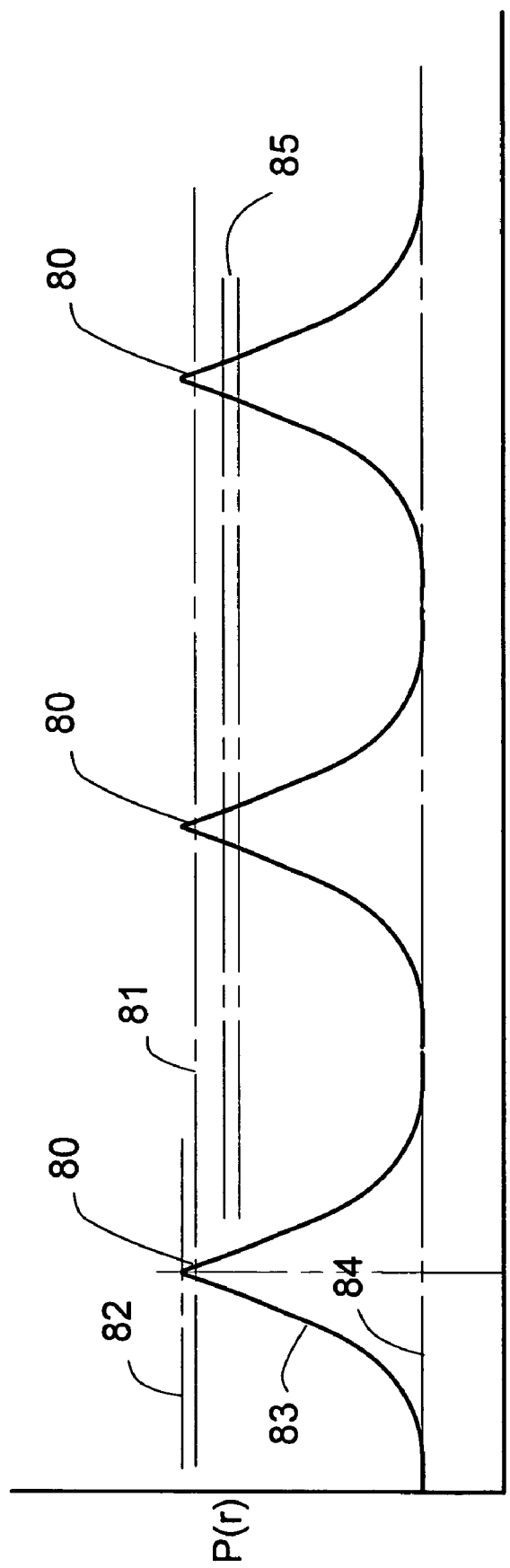
FIG. 8 is a graph of power as a function of radial dimension in an embodiment of the present invention having multiple power peaks.

In yet further alternative embodiments of the invention, the lens power distribution has a plurality of power peaks at incremental radial dimensions. One example embodiment is shown in FIG. 8 which provides a plot of power as a function of radial dimension for such an embodiment. Three optical power peaks 80 reach a maximum power 82 which is equal, or greater than, the design near vision power 81. From the apex to the first peak, the power distribution is defined in the same manner as expressed in prior embodiments. At the lens apex, the power is equal the desired distance power 84 and rises rapidly in the radial direction to affect an induced aperture. However, the power distribution 83 does not level off or flatten at the maximum power 82. The power distribution is then reflected symmetrically about the peak such that power descends in like manner to near the distance power 84. The subsequent peaks are defined by repeating this power distribution in the radial dimension. The radial location of the inner-most peak is at or within the mesopic pupillary dimension. Although FIG. 8 depicts three peaks, two, or more than three peaks may be included—the maximum being limited by the need to locate them all within the design maximum pupil dimension to be effective on vision. These power distributions having multiple peaks provide improved distance vision as a consequence of the induced aperture effect previously discussed. As well, the repeated peaks provide at least two additional benefits. The first benefit is improved intermediate and near vision due to the fact that each peak provides an incremental effective region of power 85 at intermediate and near distance powers less than the maximum power 82. An additional benefit is the consequent thinning of the lens that results from the associated lens surface shape.

Figure 9:
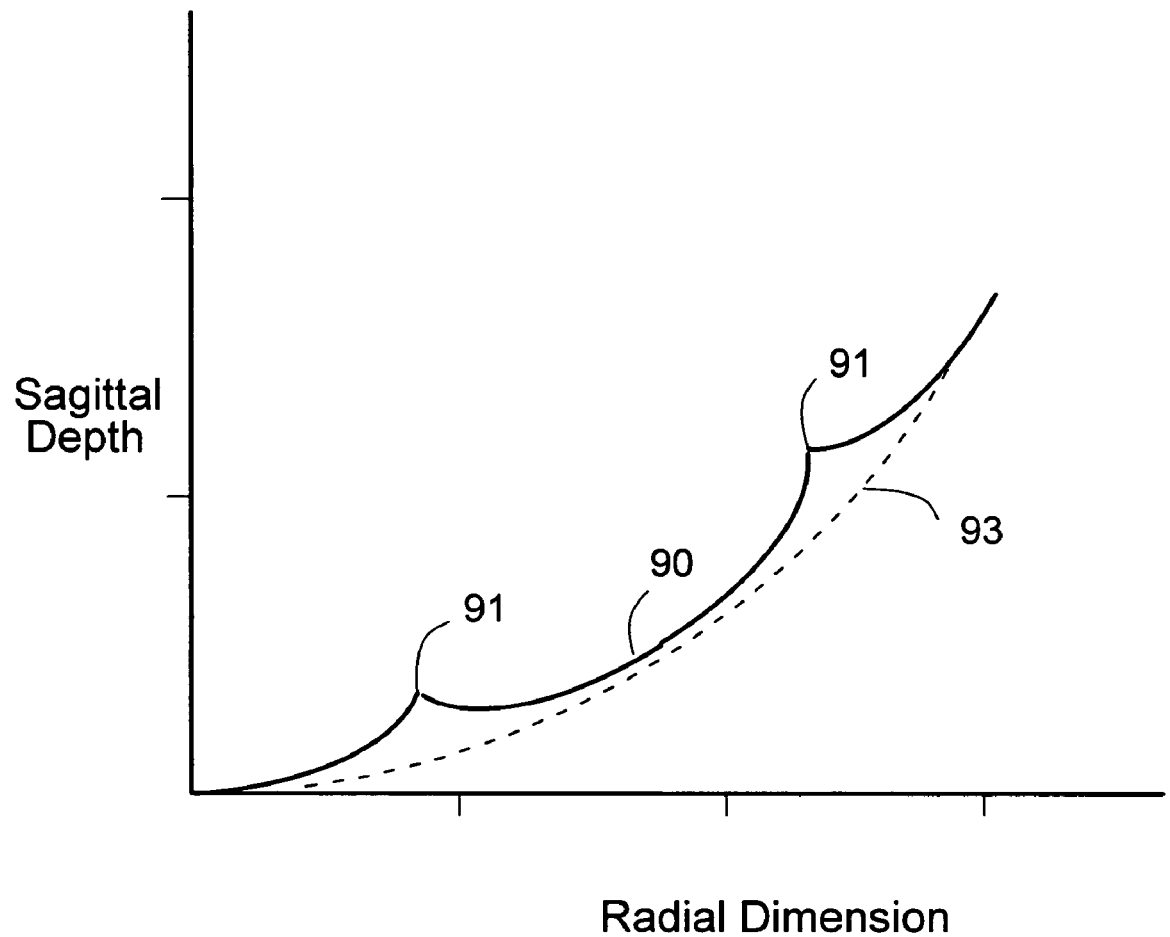
FIG. 9 depicts an axi-symmetric lens surface as a plot of sagittal depth as a function of radial dimension for the anterior optical surface of a lens having a multiple-peak power distribution according to the present invention.

FIG. 9 depicts an axi-symmetric lens surface 90 shown as a plot of sagittal depth as a function of radial dimension for the anterior optical surface of a lens. This surface provides a power distribution as described with respect to FIG. 8, but having two peaks. Each power peak is associated with a sulcus 91 in the lens surface 90. Although each sulcus is shown as having a discontinuous trough, practicalities of manufacture dictate that these will be in fact somewhat rounded or blended. Although these potentially may induce some level of diffractive interference, it is believed to be of minimal effect in most lenses. Embodiments of the invention having multiple power peaks are characterized in part by a plurality of radial sulci. At the outer radial dimensions, the thinning effect of the sulci can be seen as the lens surface follows closely the lens base curvature line 93. The lens surface shape to produce the above described power distribution between the apex and the first peak is defined in various embodiments by the equations discussed above. This shape may then be reflected symmetrically about the peak and imposed over the lens curvature using known methods. Such operations are easily carried out using modern numerically controlled lathes designed for the purpose. In alternative embodiments, the several peaks may each have a distinct surface shape. That is, one or more surface inclines, or declines, defining the individual peaks may be specified by a surface shape distinct from the other inclines and declines. For example, the surface shape from the lens apex to the first peak may be specified by Equation 5 above with a first set of parameters (i.e. values of P and S) while the surface shape declining from the first peak, and subsequent peaks, are defined by Equation 5 with a second distinct set of parameters (reflected as necessary in each case).

Figure 10:
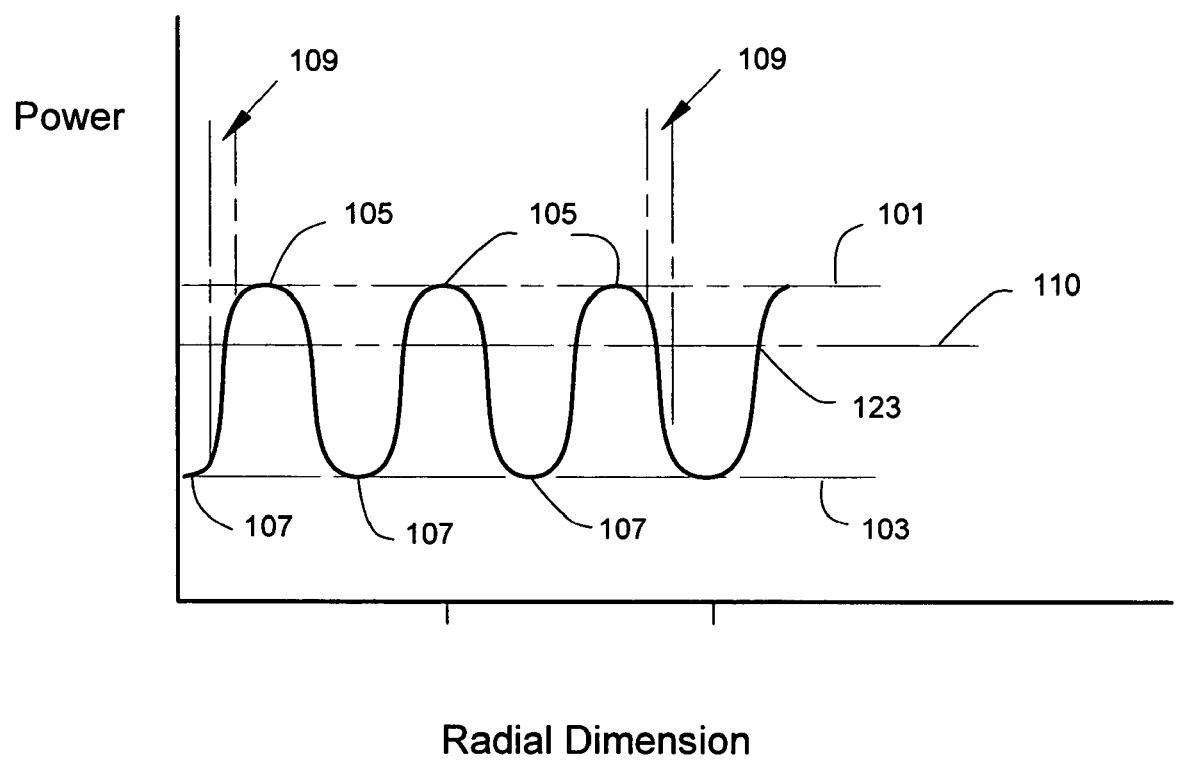
FIG. 10 depicts a power distribution of one embodiment of the invention including induced apertures at two distinct powers.

FIG. 10 depicts a power distribution of an embodiment of the invention including multiple induced apertures at two distinct powers 101, 103. The power distribution includes multiple local maximum powers and local minimum powers at powers 101, 103. The meaning of local maximum or minimum should be clear but may be determined by the following: a maximum is preceded, in the power distribution, by positive slope and followed by negative slope. The reverse identified a local minimum. Each effective local maximum 105 and local minimum 107 is bounded by steps of increasing or decreasing power. The nature of these steps is as discussed above: smooth and with rapidly changing power. In the figure, all local maximums have a maximum power associated with correction for a single specific plane-of-regard. Herein "plane-of-regard" is term indicating a spatial plane a specific distance from the subject optical surface and requiring a specified optical correction in application. For example, the plane-of-regard for what is generally considered distance viewing or sight is at infinity. Likewise, for typical near sight, the plane-of-regard is about 40 cm (centimeters) from the eye. Between these typical extremes, intermediate planes-of-regard may be of interest to a viewing subject and require distinct corrective power. In FIG. 10, two planes-of-regard are provided greatest intensity of correction. These are the associated with the optical powers of the local minimums and local maximum. If these planes are near vision and distance vision, planes-of-regard between these distances will often be provided reduced corrective power intensity. This is due to the relatively smaller incremental radial element that provides effective power at any particular point within the rapidly changing optical step 109. To increase the corrective intensity at these "intermediate" planes-of-regard the power distribution is made to repeatedly pass through the associated intermediate power 110 for each such intermediate plane-of-regard. This "redundant" power distribution provides increased intensity as a result of its integration by the human cortical vision system. Each repeated radial point of power for a plane-of-regard must be bounded by a smooth power distribution for acceptance of the produced image by the human cortical system as discussed above. Any portion of the power distribution bounded by optical discontinuity will not be effective.

In FIG. 10, each local maximum and minimum, when bounded by optical steps, will produce an induced aperture with increased clarity at the subject maximum or minimum power. In the case of nonapical maximums and minimums, the induced aperture is annular in geometry. Each of multiple induced apertures having a common maximum or minimum power contributes to the corrective effect at the associated plane-of-regard.

Figure 11:
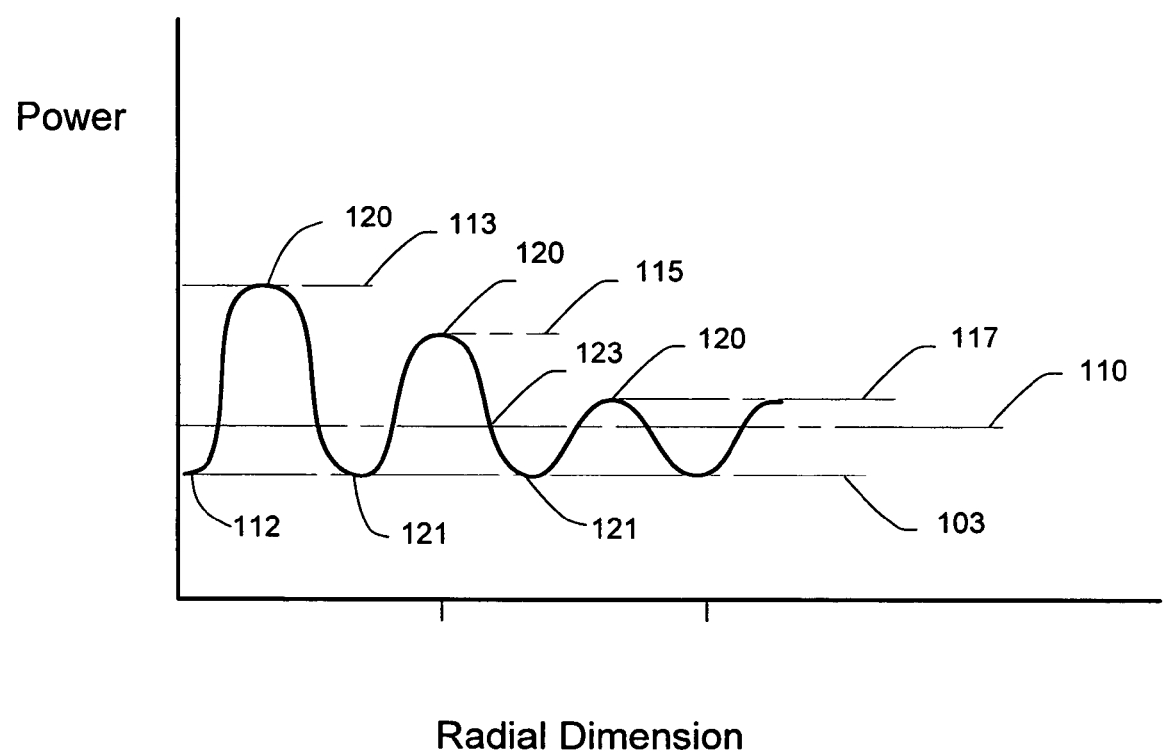
FIG. 11 depicts a power distribution of one embodiment of the invention including multiple annular induced apertures at multiple distinct powers.

FIG. 11 depicts an alternative lens power distribution according to the invention which provides an apical (center) induced aperture 112 and multiple annular induced apertures 120 directed at various planes-of-regard. The power distribution has repeated induced apertures 112, 121 at a minimum power 103 for emphasized intensity at the associated plane-of-regard. This, in application, may, for example, provide power for distance vision. Annular induced apertures are provided at three distinct power levels 113, 115, 117 directed at three distinct planes-of-regards. For example, these may be directed at near vision for distinct reading and intermediate working distances. At the same time, the repeated or redundant nature of the power distribution provides corrective power for planes-of-regard between those addressed by the induced aperture. This is accomplished, as discussed with respect to the embodiment of FIG. 10, as intermediate power 110 is repeatedly provided at radial distinct points 123 of the distribution, each contributing to correction for the associated plane-of-regard. It should be clear that the embodiments of FIGS. 10 and 11 are only examples of an infinite number of arrangements of apical and annular apertures and associated distinct powers that may be combined to address corrective needs in particular applications. Likewise, alternative embodiments include only annular apertures with no center aperture.

Figure 12:
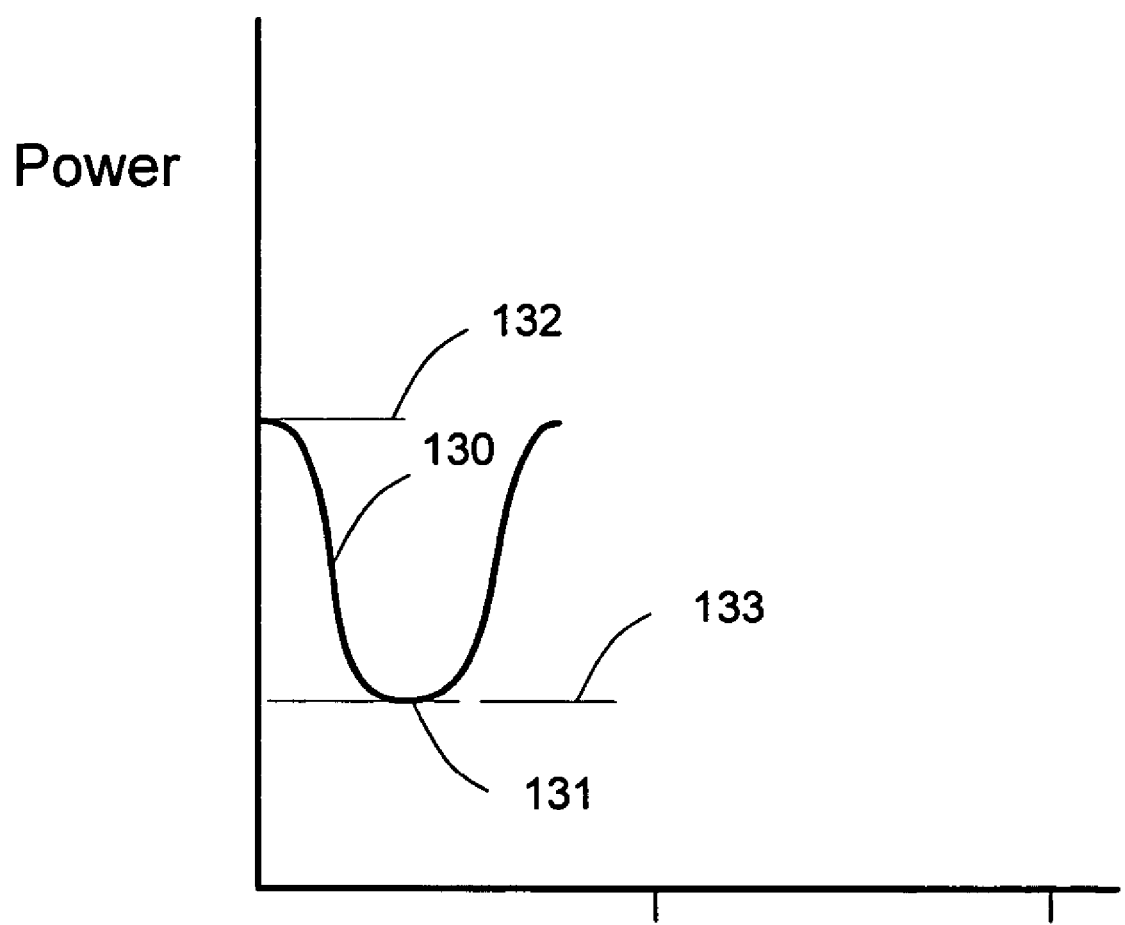
FIG. 12 depicts a power distribution of yet another embodiment of the invention having a single annular aperture with a higher apical power.

FIG. 12 depicts another embodiment of a lens according to the present invention. A power distribution 130 is shown having a single annular induced aperture 131 and a higher apical power 132. This power distribution may be employed effectively as a single focus lens to provide distance viewing correction power 133. If the apical power 132 (also the maximum power at the top of the optical step outside the aperture) is sufficiently high, it will not be accepted by the human cortical system at any plane-of-regard. This design is particularly beneficial for single focus positive lenses. The annular aperture is produced, in a positive lens, by a surface shape resulting in a more constant thickness lens. Such a lens produces significantly less spherical aberration compared to conical lenses providing the same correction. A lens with enhanced clarity and vision is thereby provided. In alternative embodiments, the apical power 132 is designed to provide correction associated with a near-sight plane-of-regard, whereby a multifocal lens is produced.

To produce an optical surface having the required power distribution, the methods discussed previously may be applied as demonstrated in the following example. To ensure that each induced aperture and intermediate power within the optical steps are effective, the power distribution is defined by a continuous function from the apex to the limit of the mesopic pupillary region. Because of their relative ease of mathematical manipulation, the many useful power distributions may be preferably derived from cyclic functions. For example, the desired initial power function may be defined as follows:

$$P(x) = P1 \cdot \left[1 + \left(\frac{P2-P1}{P1}\right) \cdot \cos\left(\frac{\pi}{1} \cdot x\right)^4\right] \quad \text{Eq. 8}$$

where
P(x) is a power at a point x
P1, P2 are defined powers

The required optical surface may be obtained in various ways. For example, the above power function may be equated to the basic expression of power in terms of curvature as in Equation 9.

$$P(x) = k \cdot \left[\frac{d^2}{dx^2} y(x)\right] \cdot \left[1 + \left(\frac{d}{dx} y(x)\right)^2\right]^{-\frac{3}{2}} \quad \text{Eq. 9}$$

This may be expanded in a Taylor series and the higher order terms dropped. Most designs require two or more terms. The result may be integrated and solved to arrive at an expression for the optical surface profile, y(x). Verification of the resulting power distribution, and adjustment by iteration, may be necessary by substitution in the original equations. It will be obvious that combinations of different cyclic functions may be used to define power distributions having various local maximum and minimum powers at induced apertures.

It will clear to one skilled in the art that other mathematical methods can be used to define power distributions and associated optical surfaces as defined by the invention. Symmetric power distributions according to the invention may be defined by multiple radially connected functions if the herein defined requirements are satisfied at all points. Additionally, the benefits of the power distributions herein described may be applied to corrective devices in combination with other optical elements.

Figure 13B:
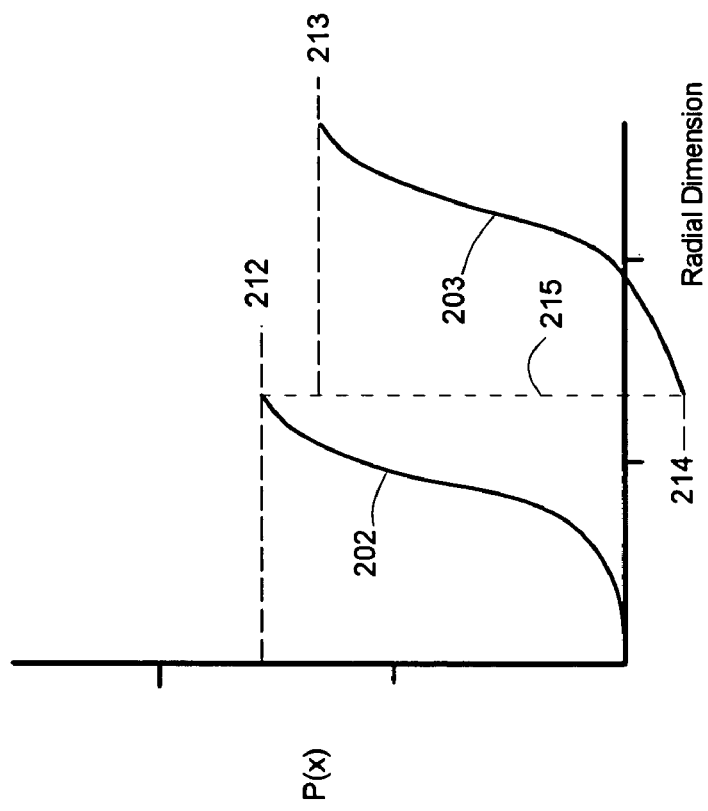
FIGS. 13A,B and 14A,B depict various power distributions with radially repeated form and multiple apertures providing redundancy at various powers.
Figure 13A:
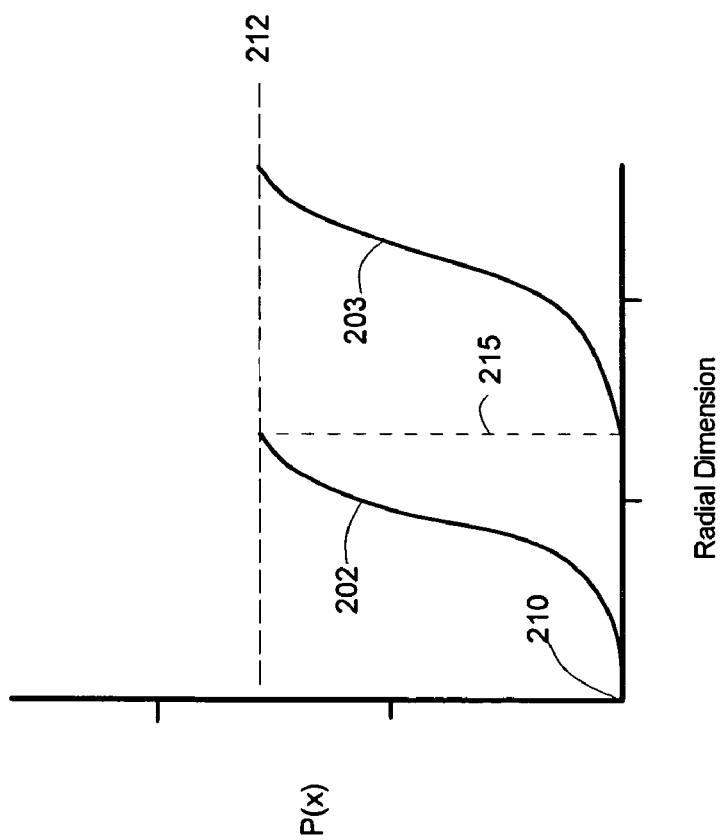

FIGS. 13A,B and 14A,B depict various additional embodiments of the invention also providing a redundant lens power distribution. The inventive lens power distribution is formed of a contiguous radial series of individual distributions having generally similar form. In the examples shown in figures, the series includes a first 202 and second 203 individual distribution. In FIG. 13A, the first individual distribution 202 has a minimum power 210 equal to the apical power, and an individual distribution form that rises rapidly and smoothly to a peak value 212 in the same manner as expressed in prior embodiments. At the apex, the power is equal to the desired distance power. The power rises rapidly to effect an induced aperture as previously described. However, as discussed with respect to the embodiments of FIG. 8, the first power distribution 202 is truncated at its outer radial extent 215 and at its peak value 212 before zero slope is reached.

It has been found that, in many cases, near vision add power provided in radially extended regions (with zero slope) that are separated from an apical distance power have a large influence on cortical resolution and inhibit distance vision to a detrimental degree. To minimize this effect, the first distribution, and subsequent, individual power distributions, should reach the desired near vision add power with non-zero slope as shown. To further enhance distance power correction, additional individual power distributions, such as the second distribution 203 extend from the outer radial extent 215 of the first distribution 202. This provides redundant power contribution to the apical power that is nearer to the apex than prior embodiments discussed. At both the inner and outer radial extents of the second, and further additional, individual power distributions, the power slope is non-zero. This is, again, to counter the large cortical influence at these radial locations discussed above. Although FIG. 13A depicts two individual distribution regions, three or more may be included—although only those within the maximum pupil dimension will be effective on vision. Though the power is abruptly changed at the beginning of each redundant power distribution, the surface of the lens is nevertheless still smooth with attendant smooth first derivatives. This type of change has been found to be well tolerated by the cortical vision system when used in combination with the other features of the inventive lens and power distributions described. As stated, the redundant power distributions are similar but may have, and preferably do have, a steeper slope than the first distribution. The second and further power distributions are defined, and may be specified, using the same methods and equations discussed respecting prior embodiments. The non-zero slope at the extents may be obtained by defining the boundary conditions appropriately, or by curve-shifting methods, or other known methods that maintain the previously defined characteristics of the inventive lenses.

FIG. 13B depicts an alternative configuration of the embodiment of FIG. 13A. A first radial power distribution 202 has form similar to that of FIG. 13A. However, the maximum and minimum powers of the second power distribution 203 differ from the first power distribution 202, and may each be higher, lower or the same as the first power distribution 202. For example, in the figure, the second individual radial power distribution 203 has a reduced minimum power 214 below the apical power and a reduced peak 213 below the first distribution peak value 212. Because the apical power is included in the second individual power distribution, a redundant contribution to distance correction power is still provided. The reduced peak 213 also provides correction at an additional distinct plane of regard as previously discussed. In other exemplary alternative configurations, the second or further additional redundant distributions, have a minimum power above the apical power of the first distribution, providing redundancy at different power levels for different planes of regard. As discussed, the second distribution, terminate at its radial extents, at the minimum power 214 and peak power 213, with non-zero power slope.

Figure 14B:
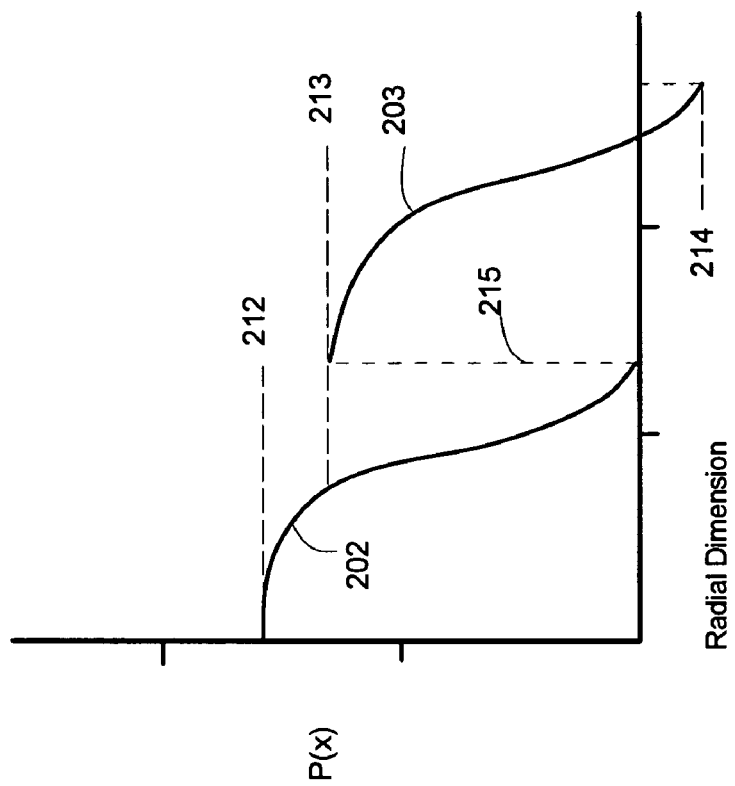
Figure 14A:
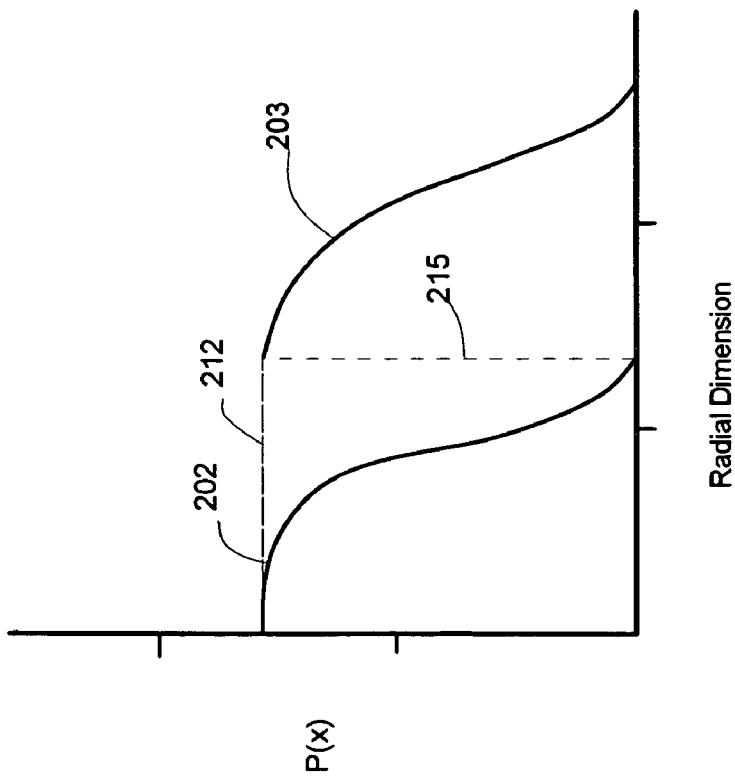

FIGS. 14A and 14B illustrate that the same concept and general design can be applied to lenses with an apical near distance power and a radially displaced distance correction region. As in the above methods and designs, applying redundant elements can be used to add emphasis to (enhance) the images from certain distances more than others. This center-near distance power configuration is somewhat favored for application to plus or convergent-focus type lenses because of the reduced spherical aberration it affords. Like the embodiments of FIGS. 13A,B, the redundant power distributions are similar, but may have duplicate powers, or reduced or higher minimum or maximum powers. In FIG. 14A, a redundant series of power distributions include a first and second individual power distribution 202, 203 that share common minimum and maximum powers. In FIG. 14B, the individual power distributions 202, 203 may have distinct powers at their radial extents in the same manner as the configurations discussed respecting FIGS. 13A and 13B.

The preceding discussion is provided for example only. Other variations of the claimed inventive concepts will be obvious to those skilled in the art. Adaptation or incorporation of known alternative devices and materials, present and future is also contemplated. The intended scope of the invention is defined by the following claims.

I claim:

1. A proximal ophthalmic lens comprising:
   an apex and apical power at the apex;
   at least one annular vision region, each of the at least one annular vision regions having a respective local maximum or minimum power; and each annular vision region bounded by optical steps having rapidly changing power; and
   an optical surface creating a power distribution that varies smoothly from the apical power at the apex and through all annular vision regions wherein said proximal ophthalmic lens is configured to be on or within an eye of the user.

2. A proximal ophthalmic lens according to claim 1, wherein:
   the apical power is a distance sight corrective power; and
   the at least one annular vision region has a near sight corrective power greater 4 than the distance sight corrective power.

3. A proximal ophthalmic lens according to claim 1; wherein:
   the at least one annular vision region comprises a first annular induced effective aperture having a distance power less than the apical power.

4. A proximal ophthalmic lens according to claim 3, wherein:
   the apical power is sufficiently high to prevent the human cortical vision system from resolving an image from any plane-of-regard passing through the apex.

5. A proximal ophthalmic lens according to claim 4, wherein:
   the apical power is more than 3.0 diopters greater than the distance power.

6. A proximal ophthalmic lens according to claim 3, wherein:
   the at least one annular vision region further comprises at least one second annular induced effective aperture having an intermediate power that is less than the apical power and greater than the distance power.

7. An ophthalmic lens comprising:
   at least one optical surface forming a symmetric smooth radial power distribution over the entire optical surface, the power distribution having at least one local maximum and at least one local minimum, all of the at least one maximum and all of the at least one minimum are each bounded by optical steps;
   the power distribution changing sufficiently rapidly in each optical step to induce a user receiving images from a plane-of-regard associated with the respective maximum and minimum to view the portion of the image passing through the optical surface at the respective maximum or minimum.

8. An ophthalmic lens according to claim 7, wherein: all local minimums have equal power.

9. An ophthalmic lens according to claim 7, wherein: all local minimums have distinct powers.

10. An ophthalmic lens according to claim 7, wherein: all local maximums have distinct powers.

11. An ophthalmic lens according to claim 7, wherein: all local maximums have equal power.

12. An ophthalmic lens according to claim 7, wherein: all maximums and minimums have mutually distinct powers.

13. An ophthalmic lens according to claim 8, wherein: the power at each minimum is a distance sight power; and at least one local maximum comprising at least one near sight region having a near sight power no more than 3.0 diopters greater than the distance sight power.

14. An ophthalmic lens according to claim 13, wherein:
   the at least one near sight region comprises an apical region.

15. An ophthalmic lens according to claim 14, wherein:
   at least one local maximum further comprising an annular induced effective aperture having an intermediate power less than the near sight power and greater than the distance power.

16. An ophthalmic lens according to claim 7, wherein:
   the power distribution is defined by at least one cyclic function.

17. An ophthalmic lens according to claim 7, wherein:
   the at least one optical surface comprises the surface of a human cornea.

18. An ophthalmic lens according to claim 7, wherein:
   the at least one optical surface is a anterior surface of a contact lens; and
   a posterior surface of the lens has a reverse geometry such that a centering force is created on the lens when fitted to an eye.

19. An ophthalmic lens comprising:
   a contact lens body having an optical surface having a symmetric radial power distribution;
   the power distribution having at least one annular induced effective aperture, each aperture having a respective local maximum or minimum power and each aperture bounded by optical steps; and
   each optical step having smoothly and rapidly changing power such that
   a user receiving images passing through the lens is induced to selectively accept the portions of the image passing through the apertures.

20. An ophthalmic lens according to claim 19, wherein;
   the power distribution is smooth from an apex to the extents of a lens mesopic pupillary region.

21. A proximal ophthalmic lens comprising:
   at least one optical surface defining:
   a first radial power distribution having an apex and an apical power at the apex and a second power at a radial extent;
   the first power distribution having rapidly and smoothly changing power from the apical power at the apex, through an optical step, to the second power at the radial extent; and
   a second radial power distribution having a respective first power at the radial extent and a respective second power at a second distribution extent;
   the second distribution having rapidly and smoothly changing power from the respective first power, through a second optical step, and to the respective second power at the second distribution extent wherein said proximal ophthalmic lens is configured to be on or within an eye of the user.

22. A proximal ophthalmic lenses, according to claim 21, and wherein:
   the first and second power distributions both have non-zero slope at their respective radial extent.

23. A proximal ophthalmic lens, according to claim 22, and wherein:
   the second power distribution first power is equal to the apical power.

24. A proximal ophthalmic lens, according to claim 22, and wherein:

the second power distribution second power is equal to the first power distribution second power.

25. A proximal ophthalmic lens, according to claim 22, and wherein:
the apical power is less than the first power distribution second power.

26. A proximal ophthalmic lens, according to claim 22, and further comprising:
at least one additional power distribution, each additional power distribution having a respective first power and a second power at a respective radial extent;
each additional power distribution having rapidly and smoothly changing power from its respective first power, through a respective optical step, and to the respective second power at the respective radial extent.

27. A proximal ophthalmic lens, according to claim 26, and wherein:
each respective additional power distribution first power equals the apical power.

28. A proximal ophthalmic lens, according to claim 26, and wherein:
each respective additional power distribution second power equals the first power distribution second power.

* * * * *